(12) United States Patent
Motsenbocker

(10) Patent No.: US 6,968,607 B2
(45) Date of Patent: Nov. 29, 2005

(54) STENT CRIMPING METHOD

(76) Inventor: Tom Motsenbocker, 3305 S. Skye Way, Flagstaff, AZ (US) 86001

( * ) Notice: Subject to any disclaimer, the term of this patent is extended or adjusted under 35 U.S.C. 154(b) by 265 days.

(21) Appl. No.: 10/623,789

(22) Filed: Jul. 21, 2003

(65) Prior Publication Data
US 2004/0093720 A1 May 20, 2004

Related U.S. Application Data

(62) Division of application No. 09/877,469, filed on Jun. 8, 2001, now Pat. No. 6,629,350.

(60) Provisional application No. 60/210,319, filed on Jun. 8, 2000.

(51) Int. Cl.[7] .............................................. B23P 11/00
(52) U.S. Cl. ............................ 29/505; 29/508; 29/515; 29/283.5
(58) Field of Search ........................ 29/505, 506, 508, 29/516, 517, 520, 243.517, 237, 283.5, 282

(56) References Cited

U.S. PATENT DOCUMENTS

| | | |
|---|---|---|
| 1,665,915 A | 4/1928 | Ekman |
| 1,889,795 A | 12/1932 | Smith et al. |
| 2,292,421 A | 8/1942 | Wolf |
| 2,751,077 A | 6/1956 | Latin et al. |
| 2,887,222 A | 5/1959 | Latin et al. |
| 3,664,213 A | 5/1972 | Anati |
| 3,695,087 A | 10/1972 | Tuberman |
| 4,413,989 A | 11/1983 | Schjeldahl et al. |
| 4,456,000 A | 6/1984 | Schjeldahl et al. |
| 4,490,421 A | 12/1984 | Levy |
| 4,578,982 A | 4/1986 | Schrock |
| RE32,983 E | 7/1989 | Levy |
| 4,854,031 A | 8/1989 | Eisenzimmer |
| 4,906,244 A | 3/1990 | Pinchuk et al. |
| RE33,561 E | 3/1991 | Levy |
| 5,026,377 A | 6/1991 | Burton et al. |

(Continued)

FOREIGN PATENT DOCUMENTS

DE       295 06 654.7       7/1995

(Continued)

Primary Examiner—Jermie E. Cozart
(74) Attorney, Agent, or Firm—Skinner and Associates

(57) ABSTRACT

An apparatus for crimping a stent by segmental radial compression, comprising a stationary base member; a rotatable drive hub which is moveable in relation to the stationary base member; and a crimping head aligned with respect to the stationary base member and to the rotatable drive hub. The crimping head includes at least ten segments. The segments each have a proximal end and an angled distal end with at least one angled side face terminating in an edge of a predetermined length, each segment having a centerline between the proximal and distal ends, each segment having a proximal point and a distal point, the distal point being disposed on the centerline and the proximal point being disposed off the centerline, and the proximal point being pivotally coupled by pins to the stationary base member and the distal point being pivotally coupled by pins to the rotatable hub member. The segments are arranged so that the segment distal ends are disposed adjacent to and a predetermined distance away from a central point and defining a central aperture with a cylindrical dimension. Also, the segment centerlines extend therefrom toward the segment distal ends and are oriented away from the central point. The segment distal ends move closer to the central point upon rotation of the rotatable hub member in a predetermined direction, whereby the stent is disposed around a base substrate, aligned in the central aperture and crimped round the base substrate upon rotation of the rotatable hub. A method of crimping a stent is also disclosed.

1 Claim, 15 Drawing Sheets

U.S. PATENT DOCUMENTS

| | | |
|---|---|---|
| 5,087,394 A | 2/1992 | Keith |
| 5,108,415 A | 4/1992 | Pinchuk et al. |
| 5,156,612 A | 10/1992 | Pinchuk et al. |
| 5,163,989 A | 11/1992 | Campbell et al. |
| 5,183,085 A | 2/1993 | Timmermans |
| 5,195,350 A | 3/1993 | Aikens et al. |
| 5,261,263 A | 11/1993 | Whitesell |
| 5,270,086 A | 12/1993 | Hamlin |
| 5,290,305 A | 3/1994 | Inoue |
| 5,304,340 A | 4/1994 | Downey |
| 5,334,146 A | 8/1994 | Ozasa |
| 5,358,486 A | 10/1994 | Saab |
| 5,381,686 A | 1/1995 | Thorup |
| 5,411,521 A | 5/1995 | Putnam et al. |
| 5,437,083 A | 8/1995 | Williams et al. |
| 5,509,184 A | 4/1996 | Herrero |
| 5,546,646 A | 8/1996 | Williams et al. |
| 5,591,222 A | 1/1997 | Susawa et al. |
| 5,626,604 A | 5/1997 | Cottone, Jr. |
| 5,628,754 A | 5/1997 | Shevlin et al. |
| 5,630,830 A | 5/1997 | Verbeek |
| 5,672,169 A | 9/1997 | Verbeek |
| 5,700,285 A | 12/1997 | Myers et al. |
| 5,725,519 A | 3/1998 | Penner et al. |
| 5,738,674 A | 4/1998 | Williams et al. |
| 5,746,644 A | 5/1998 | Cheetham |
| 5,746,764 A | 5/1998 | Green et al. |
| 5,749,921 A | 5/1998 | Lenker et al. |
| 5,766,057 A | 6/1998 | Maack |
| 5,766,203 A | 6/1998 | Imran et al. |
| 5,792,415 A | 8/1998 | Hijlkema |
| 5,807,520 A | 9/1998 | Wang et al. |
| 5,810,871 A | 9/1998 | Tuckey et al. |
| 5,810,873 A | 9/1998 | Morales |
| 5,836,952 A | 11/1998 | Davis et al. |
| 5,836,965 A | 11/1998 | Jendersee et al. |
| 5,860,966 A | 1/1999 | Tower |
| 5,893,852 A | 4/1999 | Morales |
| 5,893,867 A | 4/1999 | Bagaoisan et al. |
| 5,911,752 A | 6/1999 | Dustrude et al. |
| 5,931,851 A | 8/1999 | Morales |
| 5,951,540 A | 9/1999 | Verbeek |
| 5,992,000 A | 11/1999 | Humphrey et al. |
| 6,009,614 A | 1/2000 | Morales |
| 6,018,857 A | 2/2000 | Duffy et al. |
| 6,024,737 A | 2/2000 | Morales |
| 6,033,380 A | 3/2000 | Butaric et al. |
| 6,051,002 A | 4/2000 | Morales |
| 6,063,092 A | 5/2000 | Shin |
| 6,063,102 A | 5/2000 | Morales |
| 6,296,655 B1 | 10/2001 | Gaudoin et al. |
| 6,360,577 B2 | 3/2002 | Austin |

FOREIGN PATENT DOCUMENTS

| | | |
|---|---|---|
| DE | 195 32 288 A1 | 3/1997 |
| EP | 0 630 623 A2 | 12/1994 |
| EP | 0 701 800 A1 | 3/1996 |
| EP | 0 935 952 A2 | 8/1999 |
| WO | PCT/US95/08975 | 8/1996 |
| WO | PCT/US96/19739 | 6/1997 |
| WO | PCT/US97/20136 | 5/1998 |

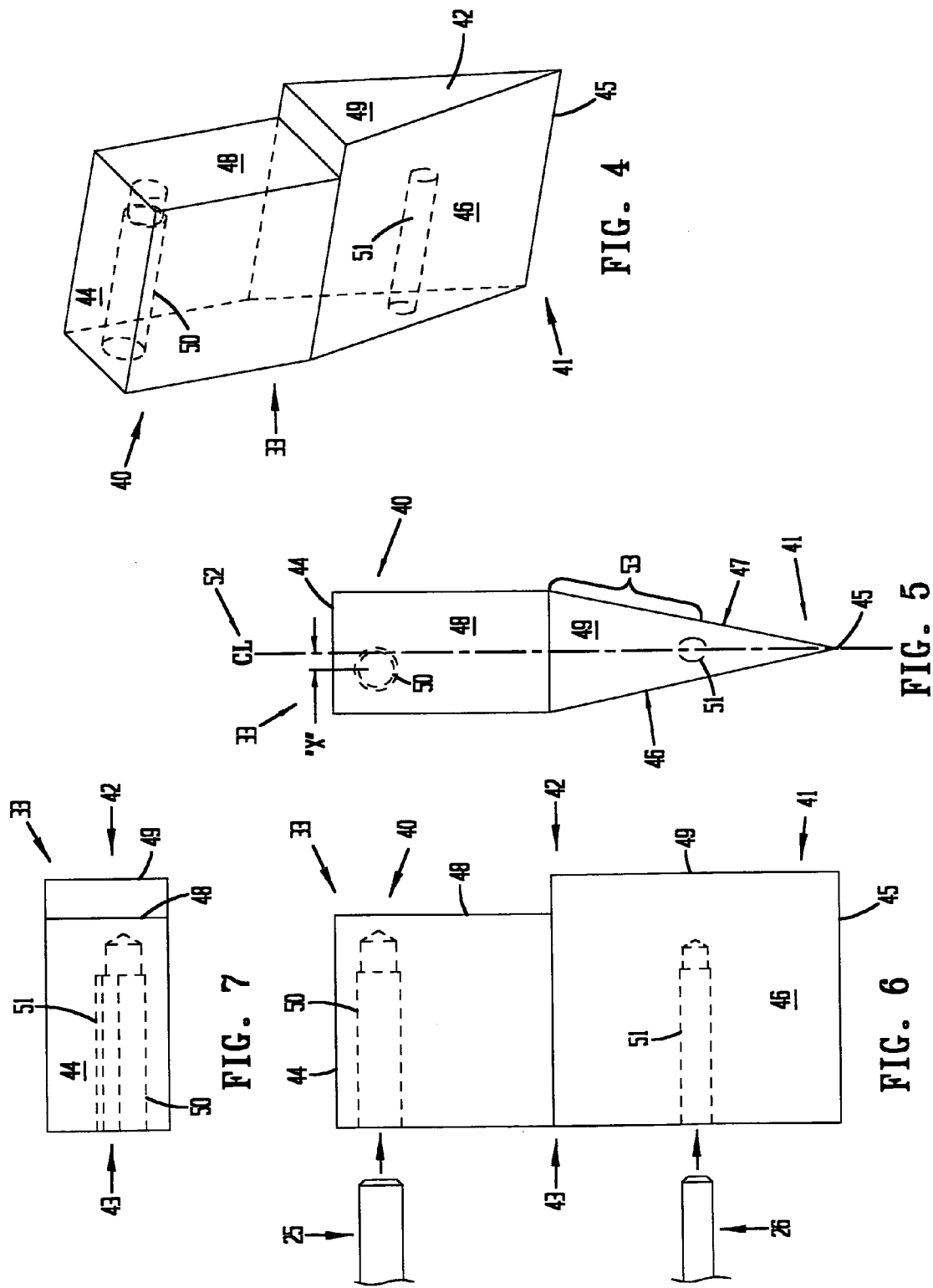

STENT CRIMPING METHOD

CROSS-REFERENCE TO RELATED APPLICATIONS, IF ANY

This application is a divisional of application Ser. No. 09/877,469, filed Jun. 8, 2001 now U.S. Pat. No. 6,629,350, which claims the benefit under 35 U.S.C. §119(e) of co-pending provisional application Serial No. 60/210,319, filed Jun. 8, 2000, which is hereby incorporated by reference.

37 C.F.R. §1.71(e) AUTHORIZATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to medical devices and medical device manufacturing apparatus and methods. Additionally, the invention relates to holding, compressing, and crimping devices. More particularly, the invention relates to medical stent crimping devices. The invention has particular utility in the medical industry as a device and method for uniformly crimping a balloon expandable or self-expanding metal or non-metallic stents or stent grafts.

2. Background Information

The state of the art includes various stent crimping devices and methods. The devices include a collet style crimp mechanism, a flat rolling plate style crimp mechanism, loop or coil radial compression (U.S. Pat. No. 6,063,102), a funnel tube style crimping mechanism (U.S. Pat. No. 5,992,000 FIG. 3), a Touhy style silicone elastomeric crimp sleeve (U.S. Pat. No. 6,009,614), and an expandable bladder/elastic tube. The flat rolling plate style crimp mechanism includes an elastomeric surface upon which the stent in place, and a flat plate positioned and adapted to roll over the stent. Weight may be added onto the plate. The rolling action crimps the stent in place somewhat akin to rolling out dough. The expandable bladder is shaped as a sleeve. Fluid is pumped into the bladder to rotatably compress the stent positioned in it. Other U.S. patents directed to stent crimping technology include U.S. Pat. Nos. 6,063,092, 6,051,002, 6,024,737, 6,018,857, 5,951,540, 5,931,851, 5,672,169, 5,672,169 and 5,626,604. These patents provide background information on stent technology in general and are incorporated by reference for that reason.

The known stent crimper devices and methods are believed to have significant limitations and shortcomings. For example, their structure (i.e. bore size in the structure) limits the diameter of the stent. Additionally, they are not able to use a simple process to satisfy the tolerance demands for certain medical applications. For example, they may not be able to accurately, consistently and uniformly crimp the stent in a single step. This is particularly true of stents with small diameters. For this and other reasons, a need exists for the present invention.

This invention provides a stent crimper device and method which are believed to fulfil the need and to constitute an improvement over the background technology. The device and method of the present invention makes it possible through a simple process to crimp a balloon expandable or self-expanding metal or non-metallic intravascular or other anatomically placed stents. The present invention does not require a fixed bore size (I.D.) to obtain the final crimped stent profile. The present invention can be designed to crimp operably receive stents having diameters from 30 mm to near zero. It has been found that, to optimize the present invention to crimp coronary stents, the device should be designed to handle stents between 0.5 mm to 5 mm. The present invention is capable of holding tolerances to 0.005" while providing a uniform extended crimp of between 1 mm and 100 mm in length.

Benefits include a reduced cycle time, reduced machine size, repeatability of the crimped stent diameter, security of the crimped stent, and the elimination of a fixed bore size (I.D.) during the crimp process.

BRIEF SUMMARY OF THE INVENTION

The present invention provides a crimping device and method which is well suited for crimping medical stents.

In one embodiment the apparatus for radially compressing an article, comprises:
  a. at least one stationary member;
  b. at least one rotatable member which is moveable in relation to the stationary member; and
  c. at least three segments;
    i. with a proximal end and an angled distal end with at least one angled side face terminating in an edge of a predetermined length, each segment having a centerline between the proximal and distal ends, each segment having a proximal point and a distal point, one said point being disposed on the centerline and one said point being disposed off the centerline, and one said point being pivotally coupled by pins to the stationary member and one said point being pivotally coupled by pins to the rotatable member;
    ii. the segments being arranged so that the segment distal ends are disposed adjacent to and a predetermined distance away from a central point and defining a central aperture with a cylindrical dimension, and that the segment centerlines extending therefrom toward the segment distal ends are oriented away from the central point; and
    iii. the segment distal ends moving closer to the central point upon rotation of the rotatable member in a predetermined direction.

The apparatus has a first state wherein the segment centerlines are tangentially oriented with respect to the central aperture, and a second state wherein the segment centerlines become radially aligned with respect to the center point and the aperture closes upon rotation of the rotatable member in the predetermined direction.

At least four basic arrangements of the proximal and distal points exists:

1. The segment distal point is on the center line and coupled to the rotatable member, and the segment proximal point is disposed off the centerline and coupled to the stationary member.
2. The segment distal point is on the center line and coupled to the stationary member, and the segment proximal point is disposed off the centerline and coupled to the rotatable member.
3. The segment distal point is off the center line and coupled to the rotatable member, and the segment proximal point is disposed on the centerline and coupled to the stationary member.
4. The segment distal point is off the center line and coupled to the stationary member, and the segment proximal point is disposed on the centerline and coupled to the rotatable member.

For each of these embodiments may be one stationary member and one rotatable member or two stationary members and two rotatable members.

The most preferred embodiment of the single stationary member, single rotatable member apparatus for crimping a stent by segmental radial compression, comprises:

a. a stationary base member;
b. a rotatable drive hub which is moveable in relation to the stationary base member; and
c. a crimping head aligned with respect to the stationary base member and to the rotatable drive hub, and including at least ten segments;
   i. the segments each having a proximal end and an angled distal end with at least one angled side face terminating in an edge of a predetermined length, each segment having a centerline between the proximal and distal ends, each segment having a proximal point and a distal point, the distal point being disposed on the centerline and the proximal point being disposed off the centerline, and the proximal point being pivotally coupled by pins to the stationary base member and the distal point being pivotally coupled by pins to the rotatable hub member;
   ii. the segments being arranged so that the segment distal ends are disposed adjacent to and a predetermined distance away from a central point and defining a central aperture with a cylindrical dimension, and that the segment centerlines extending therefrom toward the segment distal ends are oriented away from the central point; and
   iii. the segment distal ends moving closer to the central point upon rotation of the rotatable hub member in a predetermined direction, whereby the stent is disposed around a base substrate, aligned in the central aperture and crimped around the base substrate upon rotation of the rotatable hub.

The most preferred embodiment of the dual stationary member, dual rotatable member apparatus for crimping a stent by segmental radial compression, comprises:

a. a pair of aligned, stationary base members separated a predetermined distance;
b. a pair of aligned rotatable drive hubs which are moveable in relation to the stationary base member and in synchronization with each other; and
c. a crimping head aligned with respect to the base members and the drive hubs, and including at least ten segments;
   i. the segments each having a proximal end and an angled distal end with at least one angled side face terminating in an edge of a predetermined length, each segment having a centerline between the proximal and distal ends, each segment having a proximal point and a distal point, the distal point being disposed on the centerline and the proximal point being disposed off the centerline, and the proximal point being pivotally coupled by pins to the stationary base members and the distal point being pivotally coupled by pins to the rotatable hub members;
   ii. the segments being arranged so that the segment distal ends are disposed adjacent to and a predetermined distance away from a central point and defining a central aperture with a cylindrical dimension, and that the segment centerlines extending therefrom toward the segment distal ends are oriented away from the central point; and
   iii. the segment distal ends moving closer to the central point upon rotation of the rotatable hub members in a predetermined direction, whereby the stent is disposed around a base substrate, aligned in the central aperture and crimped round the base substrate upon rotation of the rotatable hub.

The invention also provides a method of compressing an article comprising the steps of:

a. providing an arrangement of a plurality of segments, each having a predetermined shape with a proximal end and an angled distal end with at least one angled side face terminating in an edge of a predetermined length, each segment having a centerline between the proximal and distal ends, each segment having a proximal point and a distal point, one said point being disposed on the centerline and one said point being disposed off the centerline, and one said point being pivotally coupled by pins to the stationary member and one said point being pivotally coupled by pins to the rotatable member, the segments being arranged so that the segment distal ends are disposed adjacent to and a predetermined distance away from a central point and defining a central aperture with a cylindrical dimension, and that the segment centerlines extending therefrom toward the segment distal ends are oriented away from the central point; and
b. placing a stent on a base substrate;
c. inserting the stent and base substrate into the central aperture; and
d rotating the rotatable member in a predetermined direction so that the segment distal ends move closer to the central point, whereby the central aperture contacts, compresses and crimps the stent onto the base substrate.

The features, benefits and objects of this invention will become clear to those skilled in the art by reference to the following description, claims, and drawings.

BRIEF DESCRIPTION OF THE SEVERAL VIEWS OF THE DRAWING

FIG. 4 is a perspective view of an individual segment of the stent crimping head which shows certain features in phantom.

FIG. 5 is a front view of the segment of FIG. 4.

FIG. 6 is a side view of the segment.

FIG. 7 is an end view of the segment.

DETAILED DESCRIPTION

The stent crimping device and method is suitable to uniformly crimp a balloon expandable or self-expanding metal or non-metallic stents or sent grafts. A crimped stent includes a core such as a balloon catheter and a sheath. The stent is uniformly crimped to the collapsed balloon along the length, preferably within a diameter tolerance of 0.005 inches. The apparatus and methods of the invention may also be used or adapted for use in securely gripping, holding and/or selectively radially compressing other articles. The apparatus and methods are also useable or adaptable for use in crease and/or fold structures such as balloons, to form a wide variety of radial compression devices (such as within a machining center so that the machinists will not have to replace collets), and to form or create a stent retention mechanism that retains the stent without applying radial forces against the balloon, thus enabling the balloon or sheath to be retracted.

Figure 1:
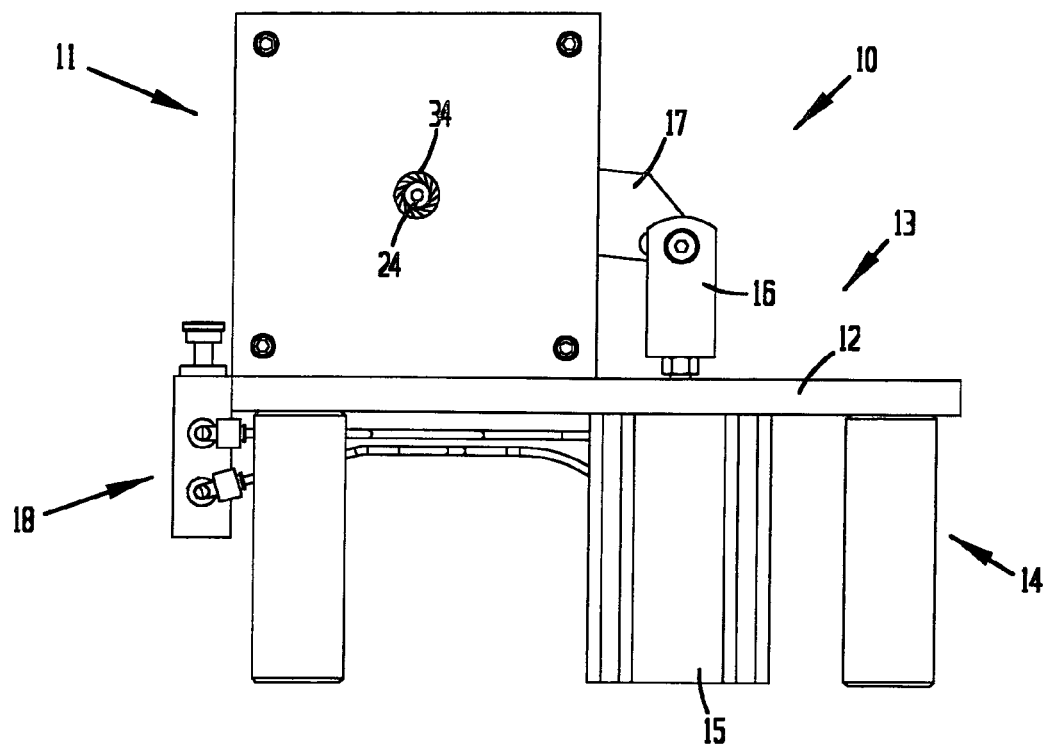
FIG. 1 is a front, plan view of a stent crimping system of the present invention.
Figure 2:
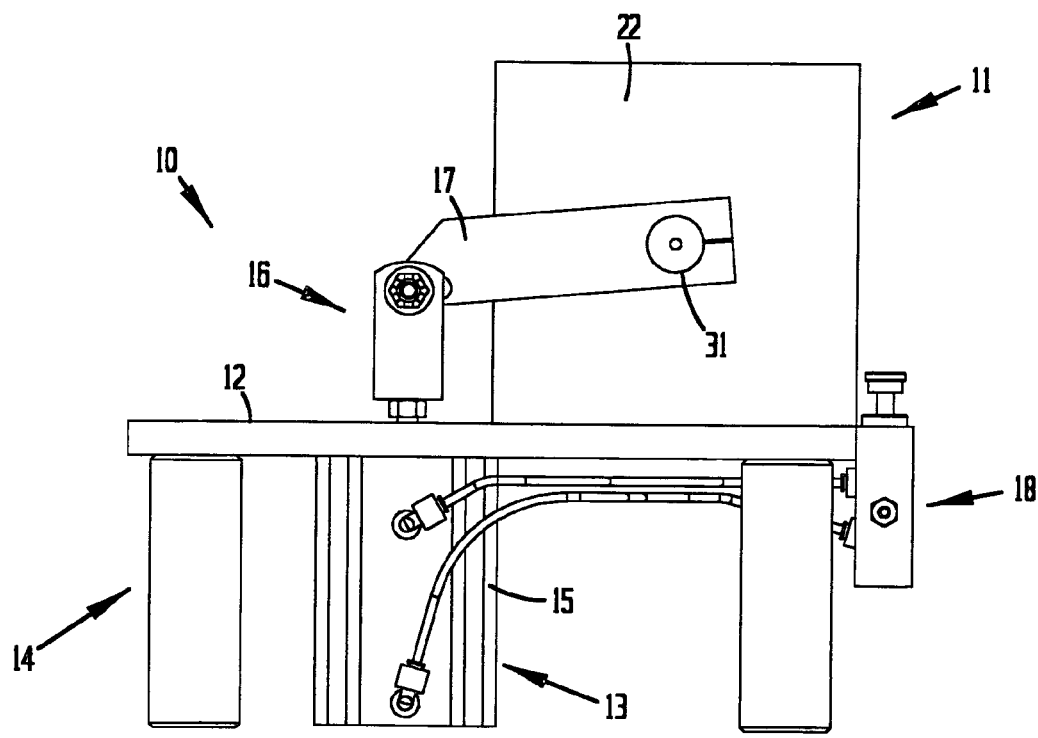
FIG. 2 is a rear or back plan view of the stent crimping system of FIG. 1.

Referring to FIGS. 1 and 2, an embodiment of the system 10 for crimping stents and the like generally includes a crimp head 11, a base 12, and an actuator 13. The crimp head 11 is disposed on the base surface 12 and primary functions to accept and crimp stents. The actuator 13 powers the crimp head. The actuator 13 preferably includes a drive mechanism 15, a linkage assembly 16 communicatively connected to the drive mechanism 15, an actuation arm 17 communicatively connected to the linkage assembly and to the crimping head 11, and an actuation control system 18 communicatively connected to the drive mechanism 15. The actuator 13 may be hand and/or foot operable by an operator. The actuator 13 is preferably a pneumatic system. Alternatively, hydraulic, mechanical, electrical, or electromechanical actuators may be used consistent with the basic teachings of the invention. The base 12 is preferably a particularized table structure having a flat work surface of a predetermined area and supported, as shown by supports or legs 14 a predetermined distance above the ground optimized for performing crimping function. It is within the purview of the invention that the crimping head 11 may be disposed on an existing table, bench or other work surface.

Additional systems, assemblies or mechanisms may be added to the basic system outlined above. These additional systems include, but are not limited to handling and alignment control and/or indication devices, pressure regulation and/or indication systems, calibration systems, control devices such as mechanical stops, vision assistance, laser micrometers, vacuum evacuation systems, interchangeable crimp heads, and crimp dwell timers. Further, the system 10 may be controlled by an operator or automated.

Figure 3:
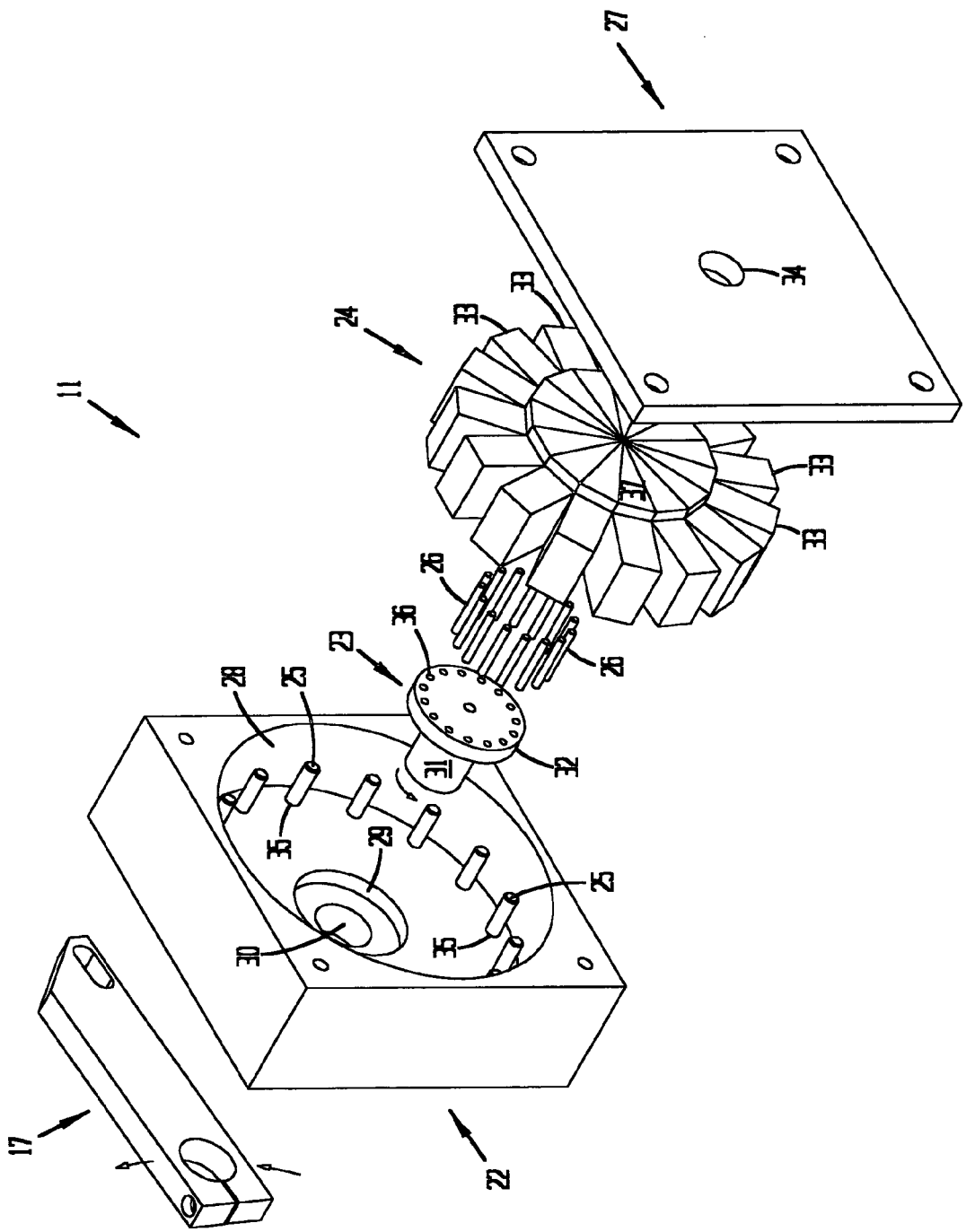
FIG. 3 is an exploded view of a crimping head utilized in the stent crimping system of FIGS. 1 and 2.

Referring also to FIG. 3, the crimp head 11 shown has a relatively compact, preferably rectilinear, configuration. The crimp head 11 basically comprises a base or housing 22, a drive hub 23, a radial compression wedge 24, a plurality of pivot pins 25, a plurality of drive pins 26, and a face plate or cover 27. The base 22 has a predetermined depth or thickness with a wedge chamber 28, a hub chamber 29, and a hub aperture 30. The hub 23 has a stem portion 31 and a plate portion 32. The wedge 24 consists of a plurality separate segments 33. The cover 27 has a centrally disposed aperture 34.

The hub 23 is constructed of rigid material, preferably metallic. The stem portion 31 of the hub 23 has a cylindrical configuration with a predetermined length and circumference such that it extends through the hub aperture 30 of the base 22. The stem portion 31 extends a predetermined distance out of the base 22 and is connected to the actuator arm 17. In this embodiment, the actuator arm 17 moves in a counter-clockwise direction during actuation to perform a holding, compressing or crimping function. The base 22 is also constructed of a rigid material, preferably metallic. The plate portion 32 of the hub 23 also has a cylindrical configuration with a predetermined depth and circumference such that it is housed within the hub chamber 29 of the base 22. The hub 23 is rotatable with respect to the base 22. When the hub plate portion 32 is operatively disposed in the hub chamber 29, its front face is approximately flush with the back wall of the wedge chamber 28. The wedge 24 has a roughly cylindrical configuration with a predetermined maximum depth and circumference such that it is housed within the wedge chamber 28 of the base 22. The cooperating depths and circumferences of the wedge 24 and wedge chamber 28 respectively, permit the wedge 24 to move within the wedge chamber 28 during a crimping operation. The pivot pins 25 are constructed of a rigid material, preferably metallic. The pivot pins 25 are cylindrical and have a predetermined length and diameter. The pivot pins 25 are preferably disposed in cylindrical slots or bores 35 in the back wall of the wedge chamber 28 of the base 22. The pins 25 are preferably held in the slots 35 via a frictional fit. The slots 35 are disposed in a circular pattern equally spaced apart a predetermined distance from each other and from the center of the wedge chamber 28. The drive pins 26 are constructed of a rigid material, preferably metallic, and have a cylindrical configuration with a predetermined length and diameter. The drive pins 26 mate with slots or bores 36 in the plate portion 32 of the hub 23. The drive pins 26 preferably have a slightly smaller horizontal dimension than that of the slots 36 to permit removal of pins 26 therefrom. Each slot 36 preferably has a cylindrical configuration which is slightly elongated along an axis extending from the center of a center of the hub 23. The slots 36 are disposed in a circular pattern equally spaced apart a predetermined distance from each other and from the center of the hub 23. The number of pivot pins 25 and drive pins 26 is equal to the number of segments 33 in the wedge 24, and each wedge 24 is associated with and pivotally coupled to one pivot pin 25 and one drive pin 26. The pivot pins 25 and drive pins 26 mate with corresponding slots or bores in the back face of the wedge segments 33. When the wedge 24 is operatively disposed within the wedge chamber 28, the face plate 27 fits over the base 22 generally flush with a raised central portion 37 of the front face of the wedge 24 formed by the segments 33.

Figure 8:
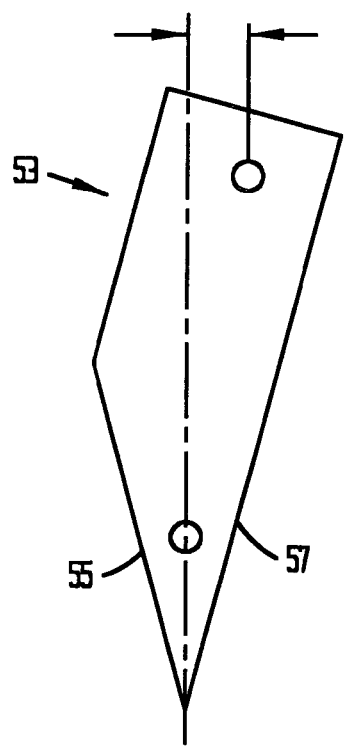
FIG. 8 illustrates an alternative embodiment of a crimping segment of the present invention with a single angle plane and a proximal offset pin aperture.
Figure 9:
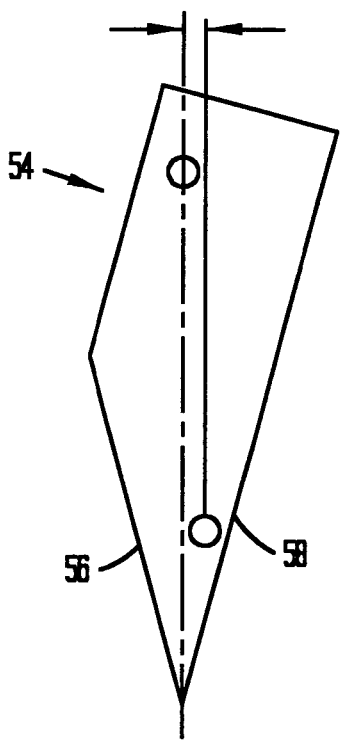
FIG. 9 illustrates an alternative embodiment of a crimping segment of the present invention with a single angle plane and a proximal offset pin aperture.

Referring to FIGS. 4–7, each segment 33 preferably has a rectilinear configuration with a proximal end 40, a distal end 41, a front face 42 and a rear face 43. A proximal end face 44 is preferably flat and rectangular with a predetermined area. The distal end 41 preferably terminates in a thin edge 45 formed at the intersection of side faces 46 and 47. Although the distal end 41 is shown to have a rectilinear, flat and uniform dimensions with a particular dimension, it may be alternatively configured with a curvilinear, non-flat, textured, and/or non-uniform surfaces (such as stepped geometries and various specialized surface textures, for example) in a variety of dimensions, including a truncated end, to provide particular gripping, compression or crimping function and depending upon the article configuration and material. The width of edge 45 is variable between approximately 5 and 100 mm and is based upon the length of the stent to be crimped or article to be engaged, held and/or radially compressed. Preferably, both side faces 46 and 47 are angled and equivalent. FIG. 5 shows optional incut portion 53 of face 47, which face is disposed away from the wedge 24 actuation direction. This provides tip angle tolerance during disactuation of the wedge 24. FIGS. 8 and 9 show alternative segment embodiments 53 and 54 wherein respective single faces 55 and 56 are angled and opposing respective faces 57 and 58 are not angled. Returning to the preferred embodiment, front face 42 has a proximal lower portion 48 and a distally oriented raised or extended portion 49. A combination of the raised portions 49 of the faces 42 of all of the segments yields center portion 37. Center portion 37 provides optimum wedge 24 stability with minimal friction.

Rear face 43 has a proximally oriented pivot slot 50 and a distally oriented drive slot 51. The center point of the pivot slot 50 is disposed a predetermined distance "X" away from a centerline 52 of the segment 33 which runs from the center distal point of the segment 33 (in this embodiment edge 45) to the center proximal point. Pivot slot 50 has a predetermined vertical depth and cylindrical configuration for mating with the pivot pin 25 which is coupled to the stationary base 22. The pivot slot 50 preferably has a predetermined diameter which is slightly greater than that of the pivot pin 25 to permit removal of the pivot pin 25 therefrom. The center point of the drive slot 51 is disposed on the centerline 52. Drive slot 51 has a predetermined vertical depth and cylindrical configuration. The drive pin 26 is preferably friction fitted into the drive slot 51. In this configuration, each drive pin 26 mates with a respective radially elongated cylindrical slot 36 of the rotatable drive hub 23. The radially elongated cylindrical slot 36 permits slight radial movement of the drive pin 26. This preferred structure provides longitudinal or radial clearance for any drive pin 26 which is not creating sufficient geometric offset in relation to an angle side 46 or 47 of a segment 33 during actuation. An acceptable alternative arrangement it to slightly radially elongate the segment 33 drive slot 51 and to construct the drive hub 23 slot 36 as a circle.

Figure 10:
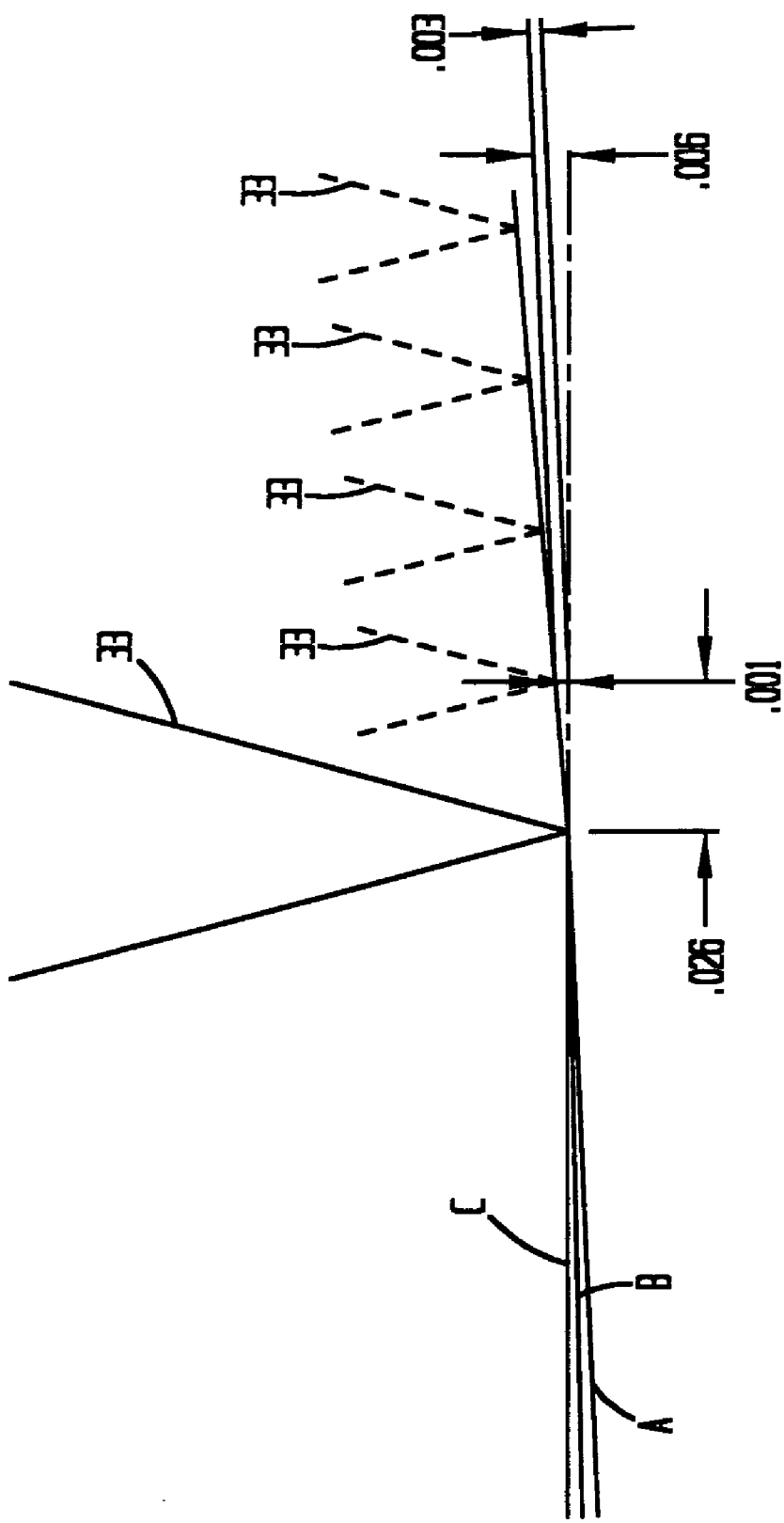
FIG. 10 is a diagram which illustrates variation in tip path of a segment with respect to different pin offset distances from a segment centerline.
Figure 11:
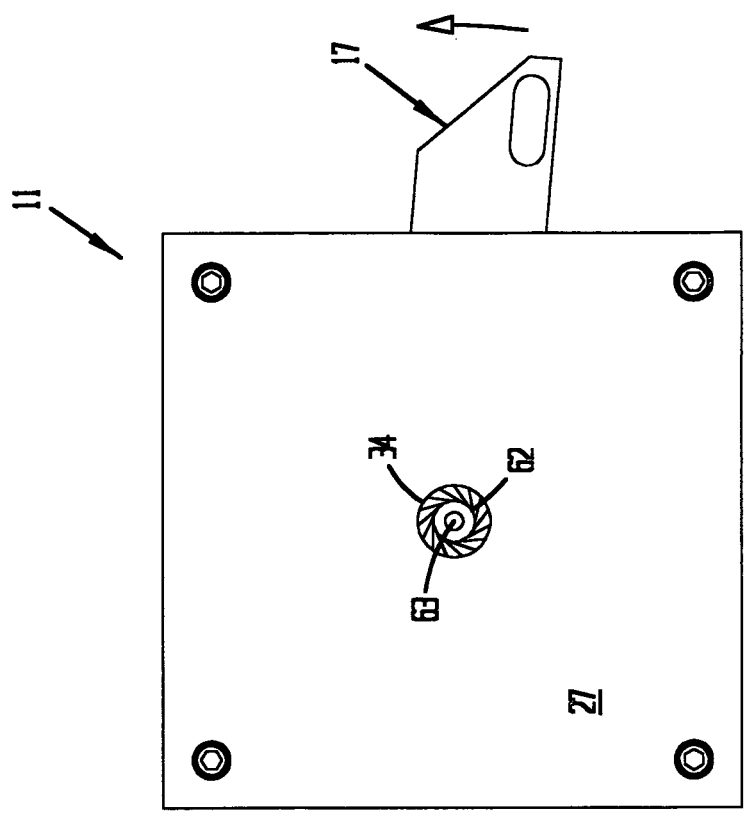
FIG. 11 is a front plan view of the stent crimping head with an access aperture in an open position.
Figure 12:
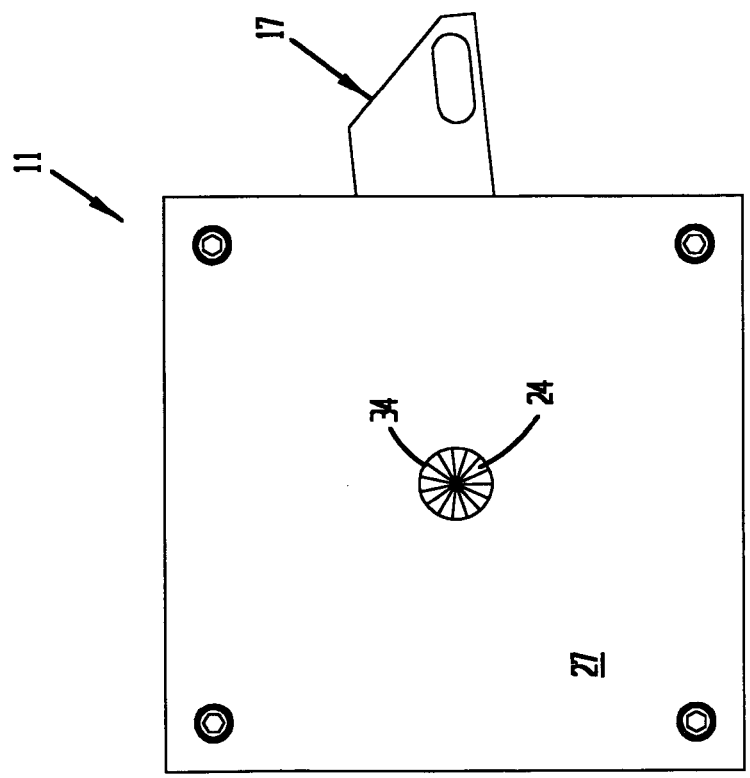
FIG. 12 is a front plan view of the stent crimping head of FIG. 11 with the access aperture in a closed position.
Figure 13:
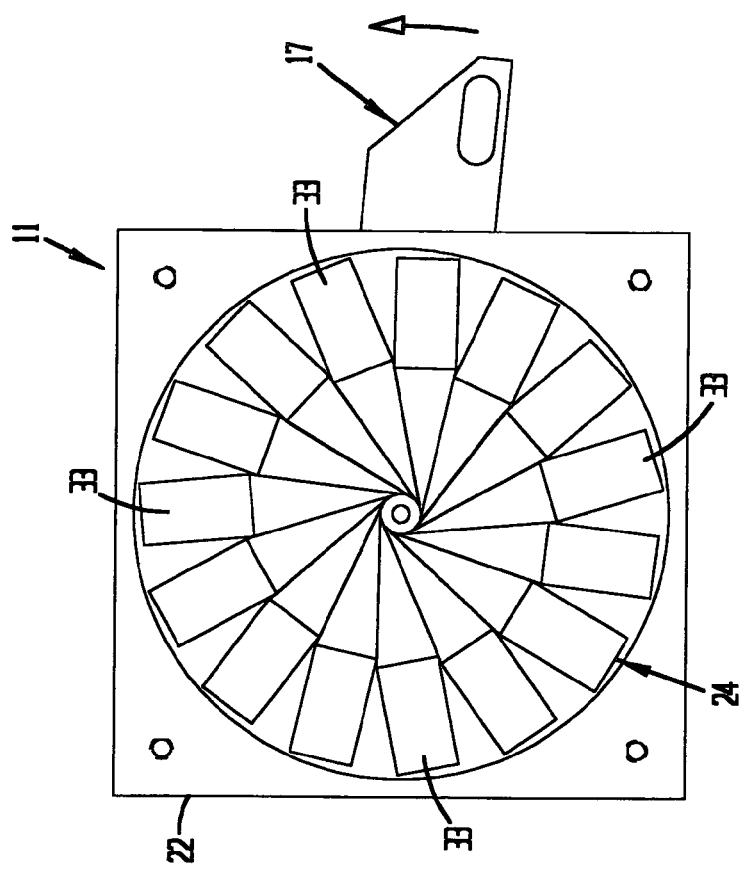
FIG. 13 is a front plan view of the stent crimping head of FIG. 11, with a face plate removed to show the position of internal segments corresponding to the open aperture of FIG. 11.
Figure 14:
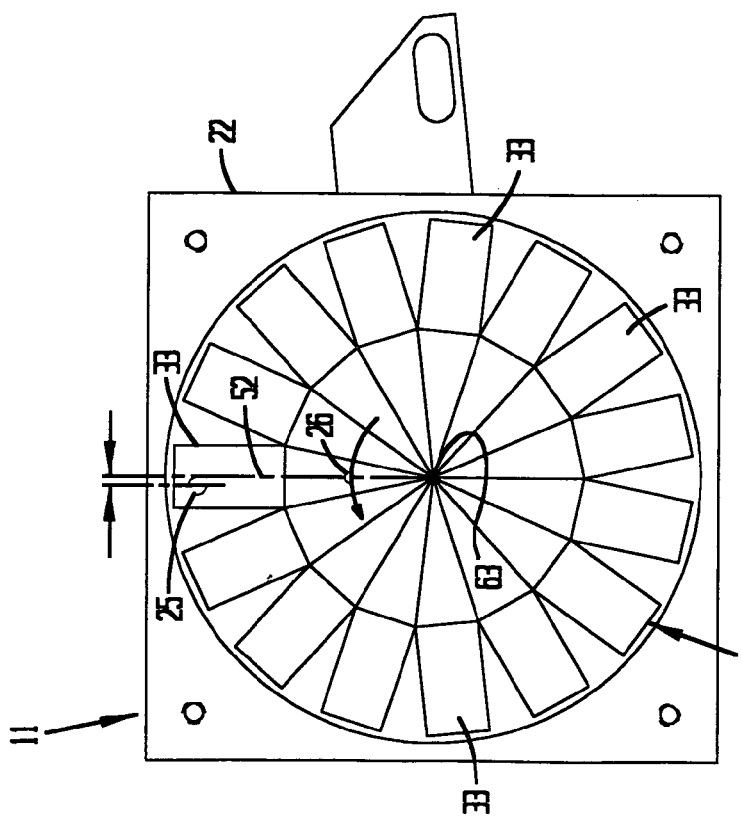
FIG. 14 is a front plan view of the stent crimping head of FIGS. 11 and 12, with the face plate removed to show the position of internal segments corresponding to the closed aperture of FIG. 12.

In general, pin offset from centerline provides tolerance for movement of the segments 33 through the operating range of the crimping wedge 24. This tolerance permits opening of the crimping head, the process of which is described below. Pivot pin 25 offset distance from centerline 52 preferably ranges from 0.05 to 0.200 inches. A preferred pivot pin offset distance is 0.050 inches for medium and large diameter crimping applications. Larger offset distances provide advantages such as reduction of tip wear and damage minimization during crimping of small diameter stents and other articles. Referring to FIG. 10, increased pin offset distances from the segment centerline decreases required tolerance at the close diameter and less segment friction within the operating range of the crimp head due to plane shifting. The tip paths of a segment with different pivot pin offset are shown. 24 degree angle planes shift back from center 0.006 at a 5 mm open position with a 0.125 inch pin offset distance. With the pin offset at 0.050 inch the tip path line is flat in comparison to a horizontal reference line. The tolerance between segments must increase with the 0.050 inch offset distance enough to reduce internal friction and concerns of wear. Tolerance allows the tips to flex and are vulnerable to damage, particularly during use with a small article. By increasing the offset to 0.125 inches, the crimp head moves freely from a working diameter of 5 mm to 0.5 mm without excessive internal friction, with reduced concerns of wear, with no increase of introduced shear, and with tightness in the closed position. The increase pin offset allows the angle planes to pull back more rapidly in relation to the actuation hub position. At a 0.052 inch open diameter, the exemplary tip is shifted back 0.001 inches. The advantage to having the segments interfere at the closed position is reduced tip flex, which allows the system to crimp onto a small diameter mandrel without segment damage. A 0.125 inch offset distance is preferable to 0.200 inch or higher offset distances due to large gaps which will occur in the open position at such offsets.

The segments 33 are preferably constructed of a polymeric material such as Delrin or Delrin AF, polycarbonate, PEEK or Ertalyte. Alternatively, they may be constructed of a thermoplastic material, a ceramic material, a composite material, or a metallic material such as stainless steel.

The segments 33 have a preferred length from distal to proximal end of about 1.5 inches, a preferred width of about 0.375 inches and preferred depths or thickness of 0.625 inches minimum and 0.750 maximum. The distal slot center is about 0.441 inches from the distal tip and the proximal slot center is about 1.375 inches from the distal tip. A preferred angle for the angled faces is about 24 degrees.

The wedge 24 embodiment shown has fifteen segments 33. The number of segments 33 is variable. Three, four, five, six, eight, 10 and 12 segment wedges are also possible depending upon the desired holding, compressing or crimping function desired and depending upon the subject article configuration and material.

Referring also to FIGS. 11–14, in operation, the wedge 24 has an initial, fully open state with centrally disposed crimping aperture 62, (best shown in FIGS. 11 and 13) a fully closed state, wherein the aperture 62 has a minimum size (best shown in FIGS. 12 and 14), and a plurality of intermediate states between the initial fully open state and the fully closed state wherein the aperture 62 becomes progressively smaller. The maximum diameter of the aperture 62 is variable up to approximately 12.0 mm. The minimum diameter is also variable, approaching zero. The length or depth of the aperture 62 is also variable between approximately 1 mm and 100 mm. A stent to be crimped or another article to be engaged and/or radially compressed is inserted and longitudinally advanced a desired distance into the aperture 62 in the initial, open state. The stent is crimped by rotating the actuation arm 17 counter-clockwise, which contracts the aperture 62. Contraction causes the aperture 62 wall to contact and exert a radially compressive force on the stent. The stent diameter is reduced a desired amount and engages a catheter body or another structure as desired in a stent manufacturing process. At the desired reduced diameter, the actuator arm 17 is held in position for a desired dwell time, typically between 0 and 20 seconds. Subsequently, the actuator arm 17 is rotated clockwise to expand the aperture 62 and release engagement of the stent. The stent and related structure is retracted and removed from the aperture 62.

Still referring to FIGS. 11–14, the crimping aperture 62 has a substantially circular horizontal dimension and a predetermined length which yields a substantially cylindrical longitudinal dimension. As the aperture 62 contracts and becomes smaller, the periphery of the aperture 62 radially moves towards the longitudinal center axis 63 of the aperture 62 in a substantially uniform manner, whereby the aperture 62 wall maintains a substantially cylindrical configuration through the closing process. Uniform compression is the result of the interaction primarily of the plurality of segments 33 and the pins 25 and 26, in concert with the respective base 22 and hub 23. In an open state, where aperture 62 exists, the centerlines 52 of the respective segments 33 do not radially extend out from the central axis point 63. During actuation, the centerlines 52 converge towards the central axis 63. In the fully closed state, the centerlines 52 extend radially outward from the central axis point 63. This process brings the distal portions 41 of the segments 33 closer to the center until ultimately the distal most portion of each segment, in this embodiment the edges 45, essentially contact the central axis point 63. Due to the symmetry of the wedge 24 elements, each segments behaves identically, and the closure process is highly uniform.

The above mentioned segmental centerline 52 convergence process result from pivotal movement of the distal portion 41 of each segment 33 with respect to the stationary proximal portion 40 of the segments 33. The drive hub 23 rotates counter clockwise with respect to the stationary base 22. The distal portions 41 of the segments 33 are moved or driven by the drive hub 23, which is pivotally coupled to each segment 33 by the drive pins 26 mated with slots 36 and 51. The proximal portions 40 of the segments 33 are held in a stationary position, but allowed to pivot, by the base 22 which is coupled to each segment 33 by the pivot pins 25 mated with slots 35 and 50.

Figure 15A:
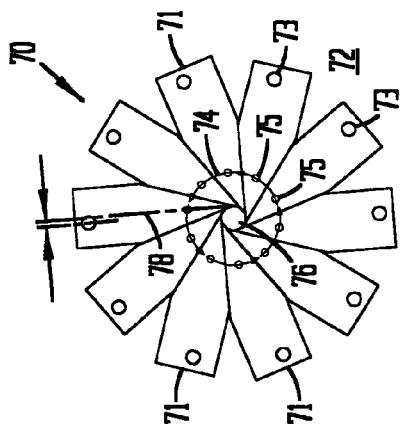
FIGS. 15A, B and C shows a sequence of movement of an embodiment of the stent crimping head as the crimping aperture proceeds from an open to a closed state, the head embodiment having a proximal offset and being distally driven.
Figure 15B:
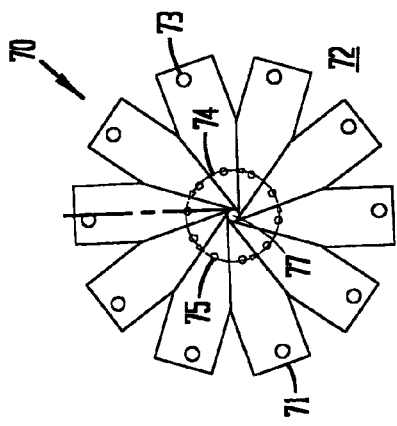
Figure 15C:
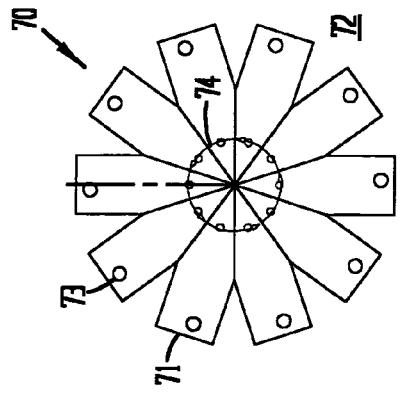

The segmental radial compression apparatus and process with distally driven, on-centerline drive pins and proximal, off-centerline pivot pins is further illustrated in FIGS. 15A–C. Wedge 70 is identical to wedge 24 of the previous embodiment except that is has 10 segments 71 instead of 15. Proximal portions of the segments 71 are pivotally coupled to a stationary base 72 by pivot pins 73 which are disposed off centerline 78 to the left (towards the direction of drive hub 74 rotation). Distal portions of the segments 71 are coupled to a driven (counter clockwise rotatable) hub 74 by drive pins 75 which are disposed on centerline 78. The drive pins 75 are permitted a slight amount of radial movement with respect to the drive hub 74 or to the segment 71 via elongated slotting previously described. FIG. 15A illustrates a first state with fully open aperture 76. The centerlines 78 of the segments 71 are not radially aligned and the distal most points of the segments are spaced from wedge's central axis. FIG. 15B illustrates a second, intermediate state wherein the hub 74 is traveling. The centerlines of the segments 71 are still not radially aligned. The distal most points of the segments are approaching wedge's central axis 77. FIG. 15C illustrates a final state where the aperture is closed. The centerlines of the segments 71 are aligned and radiate from the central axis 77. The aperture is fully closed.

Figure 16A:
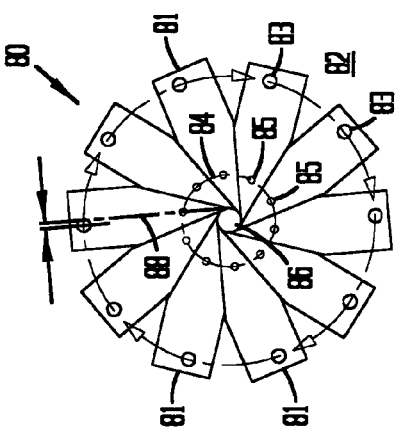
FIGS. 16A, B and C shows a sequence of movement of an alternative embodiment of the stent crimping head as the crimping aperture proceeds from an open to a closed state, the head embodiment having a proximal offset and being proximally driven.
Figure 16B:
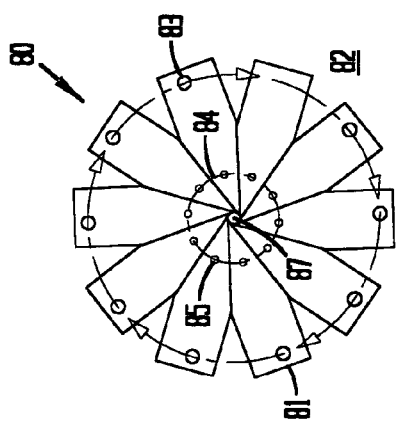
Figure 16C:
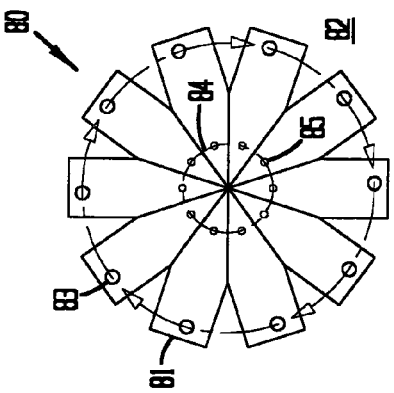

FIGS. 16A–C illustrates an alternative embodiment of the segmental radial compression apparatus and process of the present invention with proximally driven, off-centerline drive pins and distal, on-centerline pivot pins. Wedge 80 has 10 segments 81. Proximal portions of the segments 81 are coupled to a driven (clockwise rotatable) plate 82 by drive pins 83 which are disposed off centerline 88 to the left (against the direction of drive plate 82 rotation). Distal portions of the segments 81 are pivotally coupled to a stationary hub 84 by pivot pins 85 which are disposed on centerline 88. The pivot pins 85 are permitted a slight amount of radial movement with respect to the stationary hub 84 or to the segment 81 via elongated slotting previously described. FIG. 16A illustrates a first state with fully open aperture 86. The centerlines 88 of the segments 81 are not radially aligned and the distal most points of the segments 81 are spaced from wedge's central axis. FIG. 16B illustrates a second, intermediate state wherein the hub 84 is traveling. The centerlines of the segments 81 are still not radially aligned. The distal most points of the segments are approaching wedge's central axis 87. FIG. 16C illustrates a final state where the aperture is closed. The centerlines of the segments 81 are aligned and radiate from the central axis 87. The aperture is fully closed.

Figure 17A:
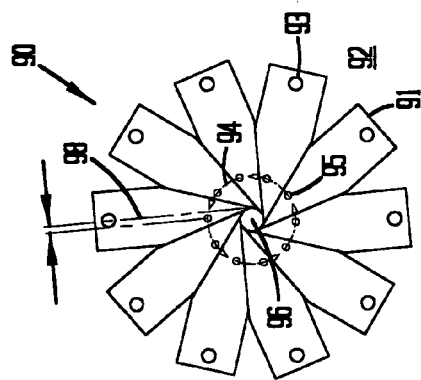
FIGS. 17A, B and C shows a sequence of movement of a further alternative embodiment of the stent crimping head as the crimping aperture proceeds from an open to a closed state, the head embodiment having a distal offset and being distally driven.
Figure 17B:
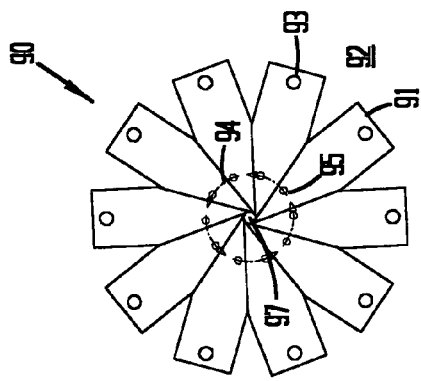
Figure 17C:
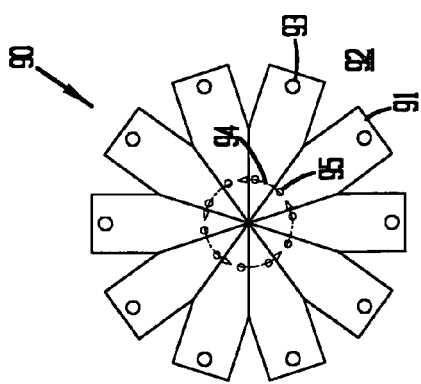

FIGS. 17A–C illustrates an alternative embodiment of the segmental radial compression apparatus and process of the present invention with distally driven, off-centerline drive pins and proximal, on-centerline pivot pins. Wedge 90 has 10 segments 91. Proximal portions of the segments 91 are pivotally coupled to a stationary base 92 by pivot pins 93 which are disposed on centerline 98. The pivot pins 95 are permitted a slight amount of radial movement with respect to the stationary base 92 or to the segment 91 via elongated slotting previously described. Distal portions of the segments 91 are coupled to a driven (counter-clockwise rotatable) drive hub 94 by drive pins 95 which are disposed off centerline 98 to the left (towards the direction of drive hub 94 rotation). FIG. 17A illustrates a first state with fully open aperture 96. The centerlines 98 of the segments 91 are not radially aligned and the distal most points of the segments 91 are spaced from wedge's central axis. FIG. 17B illustrates a second, intermediate state wherein the hub 94 is traveling. The centerlines of the segments 91 are still not radially aligned. The distal most points of the segments are approaching wedge's central axis 97. FIG. 17C illustrates a final state where the aperture is closed. The centerlines of the segments 91 are aligned and radiate from the central axis 97. The aperture is fully closed.

Figure 18A:
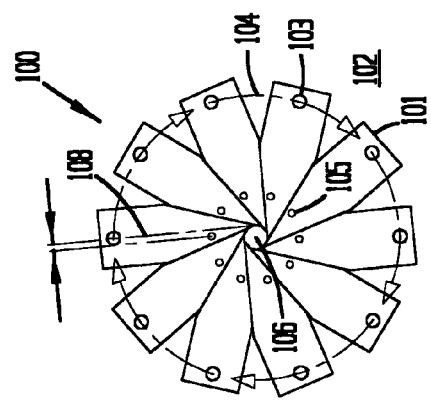
FIGS. 18A, B and C shows a sequence of movement of a further alternative embodiment of the stent crimping head as the crimping aperture proceeds from an open to a closed state, the head embodiment having a distal offset and being proximally driven.
Figure 18B:
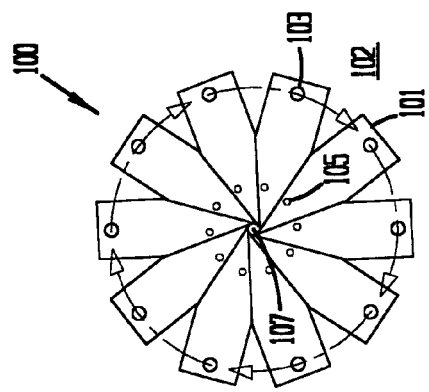
Figure 18C:
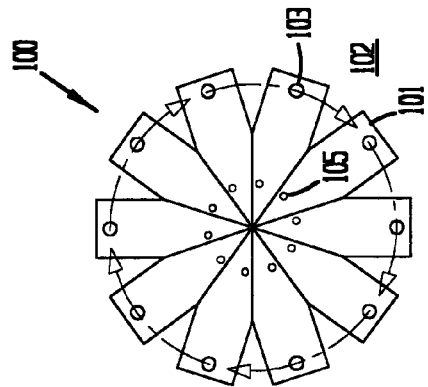

FIGS. 18A–C illustrates an alternative embodiment of the segmental radial compression apparatus and process of the present invention with proximally driven, on-centerline drive pins and distal, off-centerline pivot pins. Wedge 100 has 10 segments 101. Proximal portions of the segments 101 are coupled to a driven (clockwise rotatable) plate 102 by drive pins 103 which are disposed on centerline 108. The drive pins 103 are permitted a slight amount of radial movement with respect to the driven plate 102 or to the segment 101 via elongated slotting previously described. Distal portions of the segments 101 are pivotally coupled to a stationary hub 104 by pivot pins 105 which are disposed off centerline 108 to the left (against the direction of drive plate 102 rotation). FIG. 18A illustrates a first state with fully open aperture 106. The centerlines 108 of the segments 101 are not radially aligned and the distal most points of the segments 101 are spaced from wedge's central axis. FIG. 18B illustrates a second, intermediate state wherein the hub 104 is traveling. The centerlines of the segments 101 are still not radially aligned. The distal most points of the segments are approaching wedge's central axis 107. FIG. 18C illustrates a final state where the aperture is closed. The centerlines of the segments 101 are aligned and radiate from the central axis 107. The aperture is fully closed.

Figure 19C:
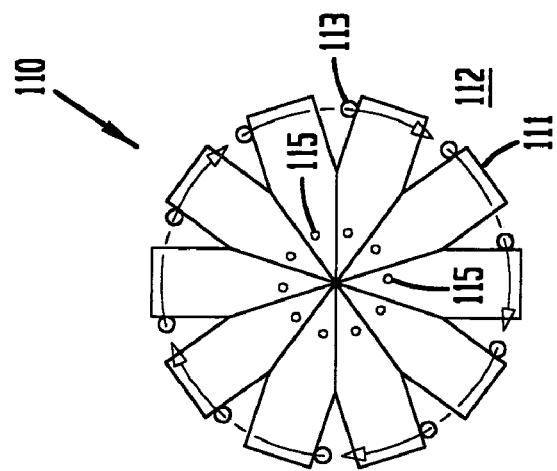
FIGS. 19A, B and C shows a sequence of movement of a further alternative embodiment of the stent crimping head as the crimping aperture proceeds from an open to a closed state, the head embodiment having a distal offset and being proximally driven by a drive pin contacting an external surface of the segment.
Figure 19B:
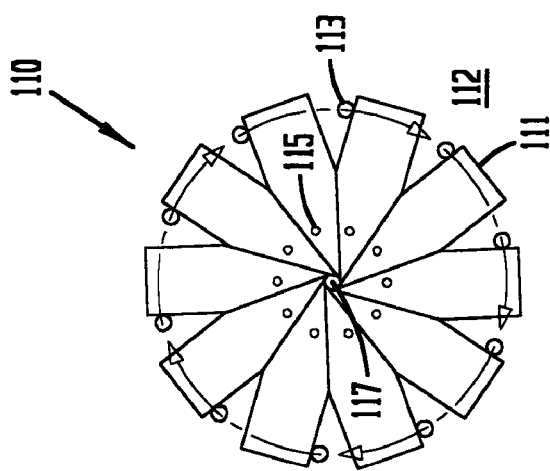
Figure 19A:
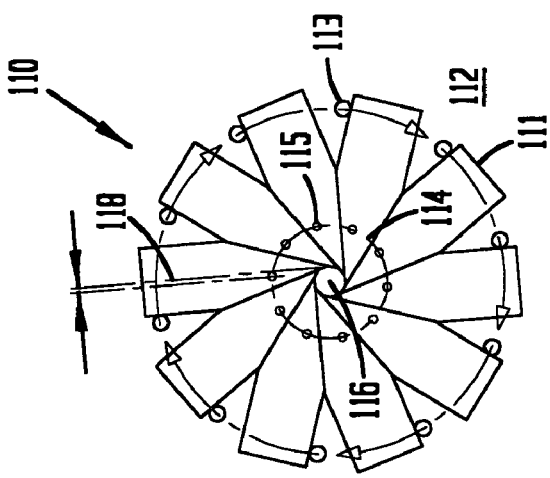

FIGS. 19A–C illustrates an alternative embodiment of the segmental radial compression apparatus and process of the present invention with proximally driven, off-centerline drive pins, which are disposed laterally to the side of the segments, and distal, off-centerline pivot pins. Wedge 110 has 10 segments 111. Proximal portions of the segments 111 are driven (clockwise rotatable) plate 112 by drive pins 113 which are disposed off centerline 118. In this embodiment, in contrast to the embodiments shown in FIGS. 19A–C, the drive pins 113 are not captured by slots in the body portions of the segments 111. Instead, the drive pins 113 are disposed to the side of the segments 111 and contact the sides of the segments at a proximal region to drive them. Distal portions of the segments 111 are pivotally coupled to a stationary hub 114 by pivot pins 115 which are also disposed off centerline 118. FIG. 19A illustrates a first state with fully open aperture 116. The centerlines 118 of the segments 111 are not radially aligned and the distal most points of the segments 111 are spaced from wedge's central axis. FIG. 19B illustrates a second, intermediate state wherein the hub 114 is traveling. The centerlines of the segments 111 are still not radially aligned. The distal most points of the segments are approaching wedge's central axis 117. FIG. 19C illustrates a final state where the aperture is closed. The centerlines of the segments 111 are aligned and radiate from the central axis 117. The aperture is fully closed.

Figure 20:
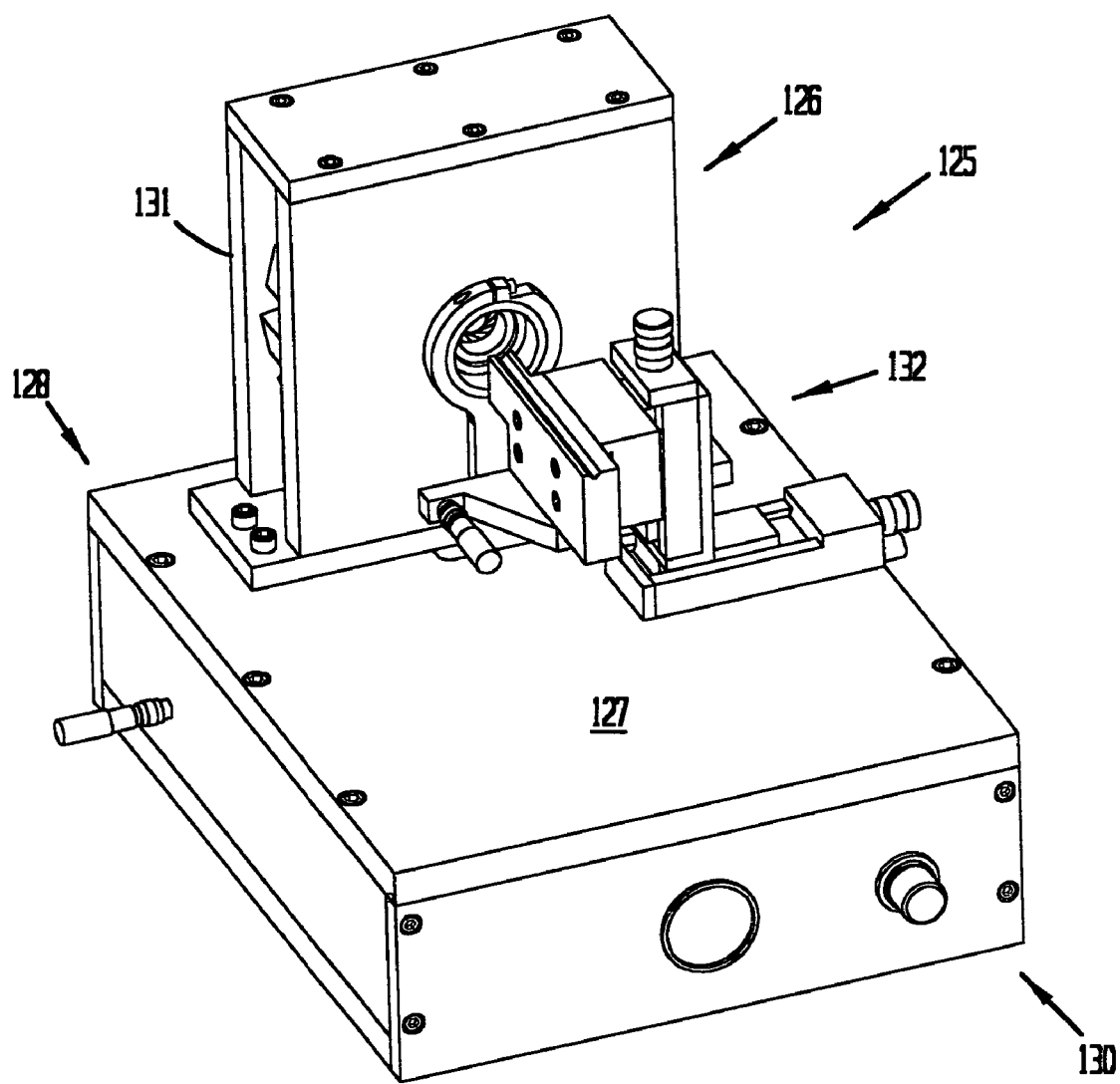
FIG. 20 is a perspective view of an alternative embodiment of the stent crimping system of the present invention, wherein the stent crimping head is actuated by a pair of actuators located at the front and back of the head.
Figure 21:
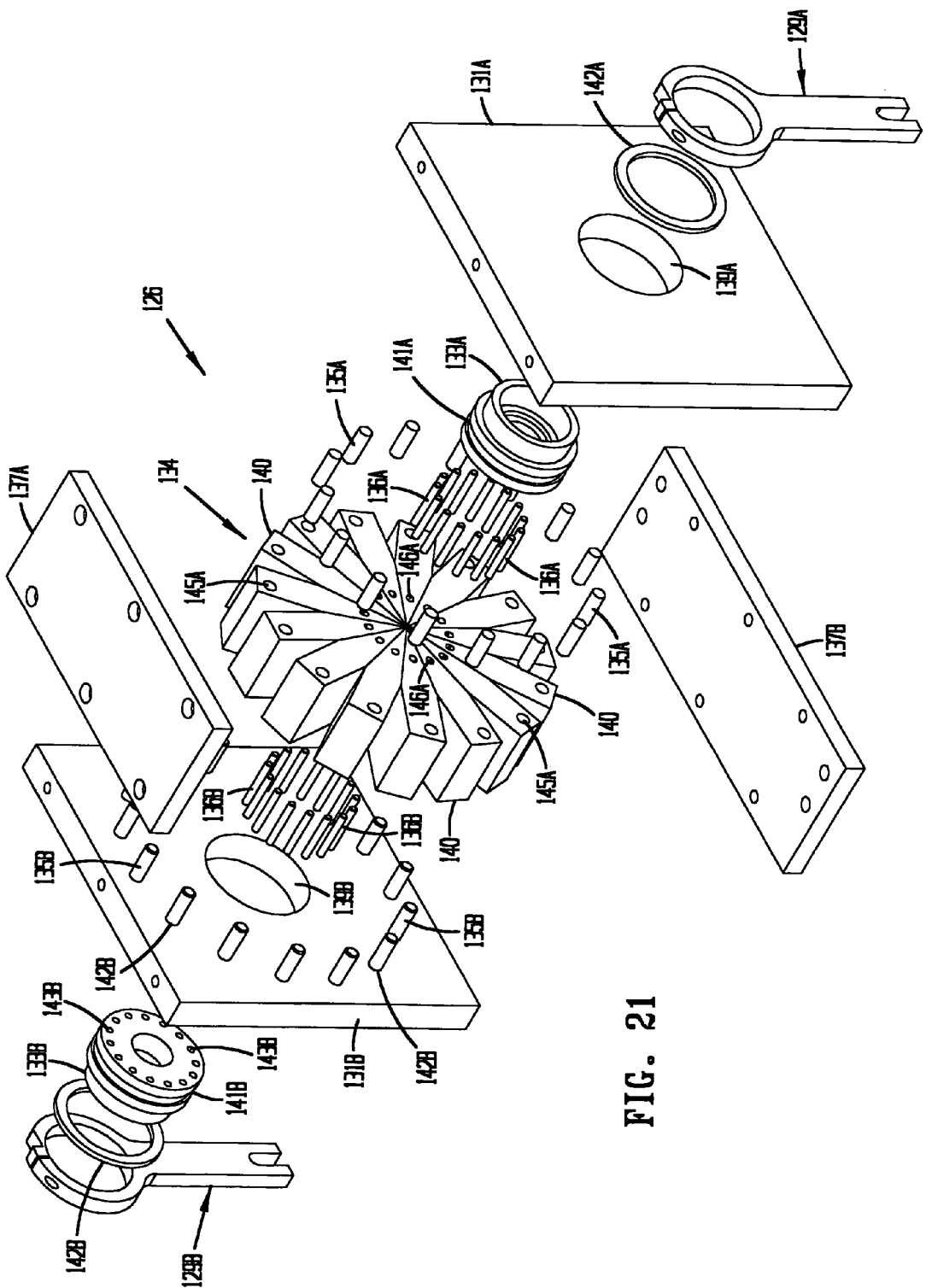
FIG. 21 is an exploded view of the crimping head utilized in the stent crimping system of FIG. 20.
Figure 22:
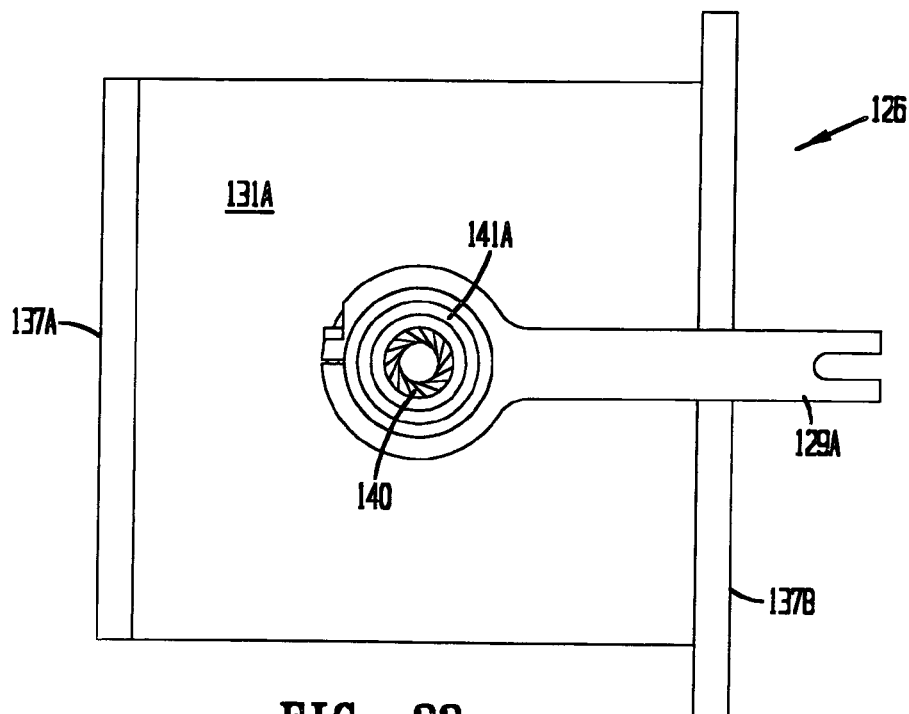
FIG. 22 is a front view of the stent crimping head of the embodiment shown in FIGS. 20 and 21, with the crimping aperture in an open position and arms a corresponding position.
Figure 23:
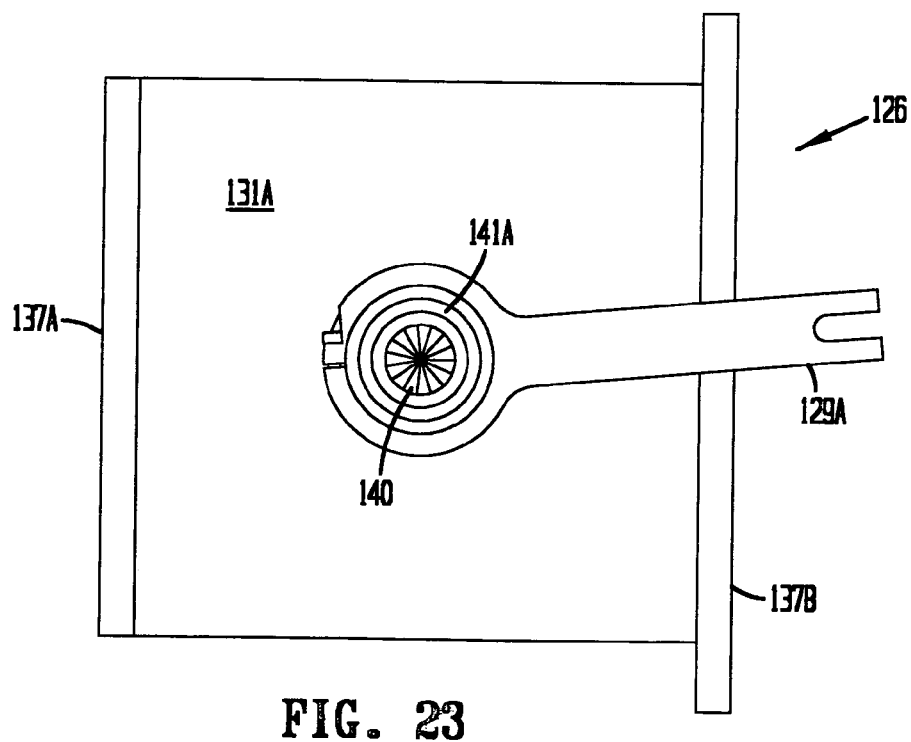
FIG. 23 is a front view of the stent crimping of dual arm embodiment with the crimping aperture in a closed position and arms in a corresponding position.
Figure 26:
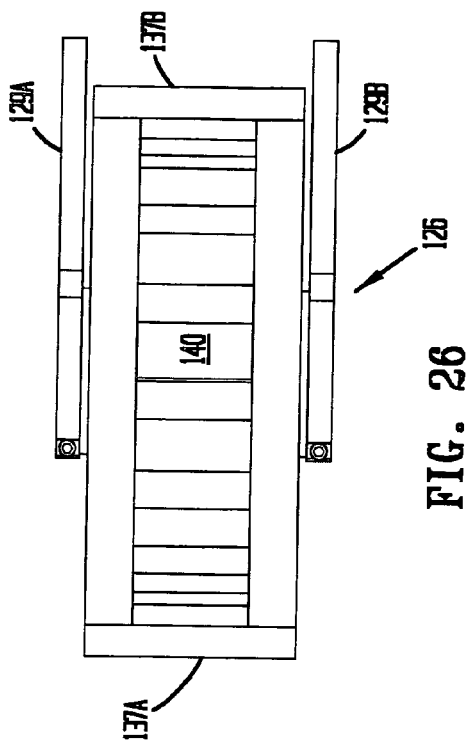
FIG. 26 is a side view of the stent crimping head of the dual arm embodiment.
Figure 25:
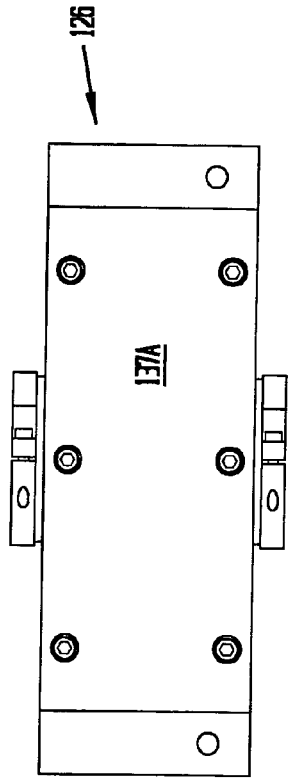
FIG. 25 is a bottom view of the stent crimping head of the dual arm embodiment.
Figure 24:
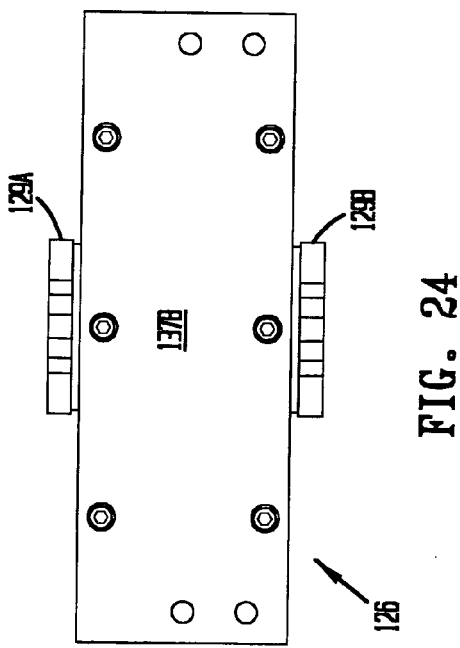
FIG. 24 is a top view of the stent crimping head of the dual arm embodiment.
Figure 27:
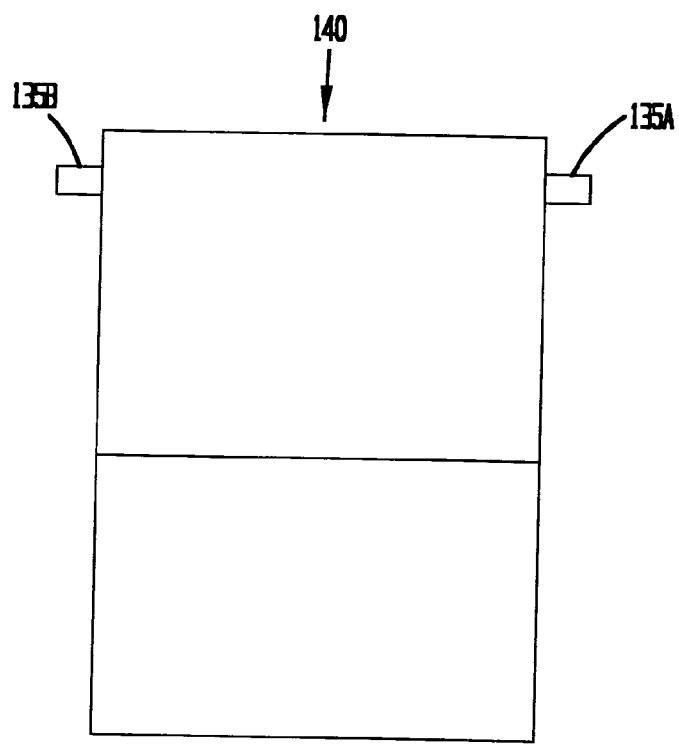
FIG. 27 shows a perspective view of an exemplary segment in the dual arm embodiment having an increased length for longer stents.
Figure 28:
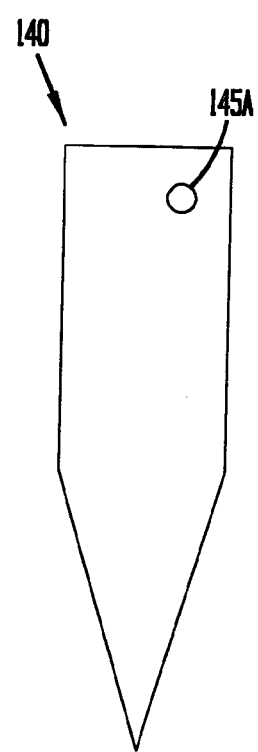
FIG. 28 shows a front view of the segment of FIG. 27.

The apparatus and methods are useable with variable width articles ranging from 0.5 mm to 5 mm to accommodate both long and short stents. To uniformly crimp a longer stent, it may be desirable to apply a crimping force at both sides of a segment. Referring to FIGS. 20 and 21, an embodiment of the system 125 for crimping relatively longer stents and the like generally includes a crimp head 126, a base 127, and an actuator 128. The crimp head 126 is disposed on the base surface 127 and primary functions to accept and crimp stents. The actuator 128 powers the crimp head 126. The actuator 128 preferably includes a drive mechanism, a linkage assembly communicatively connected to the drive mechanism, actuation arms 129A and B which are communicatively connected to the linkage assembly and to the crimping head 126, and an actuation control system 130 communicatively connected to the drive mechanism. The actuator 128 may be hand and/or foot operable by an operator. The actuator 128 is preferably a pneumatic system although other types of systems may be used. The system 125 further includes a stent handling system 132. Additional systems, assemblies or mechanisms may be added to the basic system 125.

Referring also to FIGS. 22–26, the crimp head 126 shown has a relatively compact, preferably rectilinear, configuration. The crimp head 126 basically comprises a pair of base or housing plates 131A and B, a pair of drive hubs 133A and B, a radial compression wedge 134, two sets (each set including a plurality of pins, preferably 15) of pivot pins 135A and B, two sets of drive pins 136 A and B, and a pair of separator plates 137A and B of a predetermined width which couple the base plates 131A and B. The base plates 131 have a predetermined thickness with a central hub apertures 139A and B. The hubs 133 have an annular configuration with a flat face portion. The wedge 134 consists of a plurality separate segments 140.

The hubs 133 are constructed of rigid material, preferably metallic. The hubs 133 are preferably connected to respective annular roller bearings 141A and B. The hubs 133 are connected to respective actuator arms 129 A and B, preferably via respective thrust washers 144A and B. In this embodiment, the actuator arms 129 move in a counter-clockwise direction during actuation to perform a holding, compressing or crimping function. The base plates 131 are also constructed of a rigid material, preferably metallic. The hubs 133 are rotatable with respect to the base plates 131. The wedge 134 has a roughly cylindrical configuration with a predetermined maximum depth and circumference such that it is housed between the base plates 131. The pivot pins 135A and B mate with respective, aligned pivot slots 142 A and B in base plates 131A and B, and further to respective, aligned pivot slots 145A and B in the front and rear faces of the segments 140 (at their proximal ends). The drive pins 136A and B mate with respect, aligned drive slots 143A and B in the drive hubs 133A and B, and further to respective, aligned drive slots 146A and B in the front and rear faces of the segments 140 (at their distal ends).

System 125 shown in FIGS. 20–28 functions in a similar manner to that of system 10 shown in FIGS. 1–3. In a normal mode, the actuation arms 129A and B are synchronized to move together to apply a uniform force along the entire edge of each of the relatively large wedges 140. Alternatively, the actuation arms 129A and B may be differentially actuated to provide a variable compression along the length of the wedges 140.

The crimping apparatus and method of the present invention is adaptable with thermal capability to operate at temperatures ranging between 37° C. and 300° C. by placing heater cartridges in the segments through its back. This may be used to heat set stainless steel balloon expandable stents. The stent crimping devices 10 and 125 are adaptable to compensate for thermal expansion. Further, the apparatus and methods are adaptable with cryo capability to operate at temperature ranging between −200° C. and −37° C. Liquid nitrogen my be used to cool the segments or to cool the housing plates. Alternatively, the entire head may be placed in a cryo chamber. The cryo capability may be used for Nitinol self-expanding stents. The colder temperatures causes the crimped Nitinol stent to stay at the reduced diameter. Additionally, it is believed that the colder temperatures makes Nitinol more malleable which reduces fatigue.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A method of compressing an article comprising the steps of:
    a. providing an arrangement of a plurality of segments, each having a predetermined shape with a proximal end and an angled distal end with at least one angled side face terminating in an edge of a predetermined length, each segment having a centerline between a proximal and distal ends, each segment having a proximal point and a distal point, one said point being disposed on the centerline and one said point being disposed off the centerline, and one said point being pivotally coupled by pins to the stationary member and one said point being pivotally coupled by pins to the rotatable member, the segments being arranged so that the segment distal ends are disposed adjacent to and a predetermined distance away from a central point and defining a central aperture with a cylindrical dimension, and that the segment centerlines extending therefrom toward the segment distal ends are oriented away from the central point; and
    b. placing a stent on a base substrate;
    c. inserting the stent and base substrate into the central aperture; and
    d. rotating the rotatable member in a predetermined direction so that the segment distal ends move closer to the central point, whereby the segment distal ends contact, compress, and crimp the stent onto the base substrate.

* * * * *